United States Patent [19]

Schoonen et al.

[11] Patent Number: 5,174,291
[45] Date of Patent: Dec. 29, 1992

[54] PROCESS FOR USING A MEASURING CELL ASSEMBLY FOR GLUCOSE DETERMINATION

[75] Inventors: Adelbert J. M. Schoonen; Franciscus J. Schmidt, both of Groningen, Netherlands

[73] Assignee: Rijksuniversiteit te Groningen, Netherlands

[21] Appl. No.: 474,794

[22] Filed: May 15, 1990

[30] Foreign Application Priority Data

Oct. 5, 1987 [NL] Netherlands .................. 8702370

[51] Int. Cl.$^5$ .................................................. A61B 5/00
[52] U.S. Cl. .................................. 128/632; 128/637; 435/14
[58] Field of Search ............. 128/632, 635, 637, 760, 128/762, 767, 771, DIG. 13; 604/29, 82, 83; 435/14

[56] References Cited

U.S. PATENT DOCUMENTS

| | | | |
|---|---|---|---|
| 3,785,772 | 1/1974 | Coggeshall | 128/632 |
| 4,311,789 | 1/1982 | Nylen et al. | 435/10 |
| 4,445,514 | 5/1984 | Osterholm | 128/632 |
| 4,685,463 | 8/1987 | Williams | 128/632 |

FOREIGN PATENT DOCUMENTS 0134758  3/1985  European Pat. Off. ............ 128/632

OTHER PUBLICATIONS

Kondo et al., "A Miniature Glucose Sensor, Implantable in the Blood Stream", Diabetes care, May 1982, pp. 218-220.

Primary Examiner—David M. Shay
Attorney, Agent, or Firm—Peter L. Michaelson

[57] ABSTRACT

A wearable-type glucose sensor for continuously or intermittently determining the glucose content comprises a short hollow fiber (2) to be positioned in the subcutaneous tissue. This hollow fiber is connected via tubes (3,4) with component parts (5 . . . 12) located outside the body, such as a measuring unit (11). When a perfusion fluid containing the enzyme glucose oxidase is passed through the hollow fiber, a subcutaneous dialysis will take place in which some glucose dissolves in the perfusion fluid through the wall of the hollow fiber. This glucose is completely oxidized by the oxygen dissolved in the perfusion fluid in the presence of the glucose oxidase. By means of the measuring unit the resultant amount of $H_2O_2$ or, preferably, the employed amount of $O_2$ is determined, both of which are a measure of the subcutaneous glucose concentration.

4 Claims, 11 Drawing Sheets

PROCESS FOR USING A MEASURING CELL ASSEMBLY FOR GLUCOSE DETERMINATION

The invention relates to a process for continuously or intermittently determining the glucose concentration in subcutaneous tissue, which comprises using an enzymatic oxidation of glucose by oxygen in the presence of the enzyme glucose oxidase and determining the used amount of oxygen or the resultant amount of hydrogen peroxide by means of a measuring cell.

The invention further relates to a system for continuously or intermittently determining the glucose concentration in subcutaneous tissue as well as to a measuring cell assembly suitable for use in this system and to an assembly for continuously or intermittently regulating the glucose concentration in blood.

More in particular, the invention relates to a system referred to hereinafter as glucose sensor which, e.g., could be used to control wearable-type insulin pumps. At present the number of persons provided with wearable-type insulin pumps is still limited. In general, these are people with whom the classical method of injecting insulin once or twice a day cannot provide satisfactory regulation The present wearable-type insulin pumps, however, lack the possibility of regulating the insulin dose depending on the glucose concentration in the blood. A reliable and wearable-type glucose sensor would permit a better and more comfortable regulation of the glucose concentration not only for this group of persons but also for other diabetics, and in general for persons having a need for medicines, such as insulin, depending on the glucose concentration in the blood, it would be a useful alternative Several research groups are engaged in the development of a glucose sensor. One of those research groups is the group of Shichiri of the "First Department of Medicine" at the university of Osaka, Japan. This group succeeded [see Diabetologia 24 (1983) 179-184; Biomed. Biochim. Acta 43 (1984), 561-568; Diabetes Care 9 (1986) 298-301] in developing a glucose sensor capable of measuring the glucose concentration in subcutaneous tissue for three days. The small needle-type glucose sensor consists of a platinum electrode covered with immobilized enzyme glucose oxidase. In the reaction of glucose with oxygen in the presence of the enzyme $H_2O_2$ is released which can be measured by this electrode and is a measure of the amount of glucose present. In vitro the electrode gives a current of $1.2\pm0.4$ nA in a 5.5 mmol/l glucose solution. The current is linear with the glucose concentrations, and the time required to obtain 90% of the plateau value is $16.2\pm6.2$ sec.

In the first instance, subcutaneous measurements were carried out in dogs, the response sustaining a delay of 5-15 minutes with respect to the direct measurement in blood. The sensitivity of the electrode gradually decreases to $57.4\pm7\%$ of the initial value after 96 hours measurement. This loss of signal, due to the rapid breakdown of the enzyme, causes that the subcutaneously inserted sensor must be replaced at least every three days.

Finally, Shichiri developed a completely wearable artificial endocrine pancreas ($12\times15\times6$ cm, 400 g) consisting of the sensor, a microcomputer which calculates the required infusion rate of insulin, and a dual-syringe driving system. This apparatus is capable of regulating the blood glucose concentration in depancreatized dogs for three days. Then Shichiri proceeded in measurement in subcutaneous tissue of diabetics. The subcutaneously measured glucose values are, cn an average, 10% lower than those of blood, but there is a good correlation between the two values.in the range of from 60 to 400 mg/dl glucose. The complete artificial pancreas was then tested out on diabetics, using a self-developed subcutaneous nsulin infusion algorithm Mention is only made of one representative patient in which the glucose was regulated with the sensor for two days.

Another research group was directed by M. Kessler of the institute for physiology and cardiology of the university of Erlangen-Nuremberg. The glucose sensor developed there [Hepato-gastroenterol. 31 (1984) 85-288] also functions via an enzymatic conversion of glucose by means of glucose oxidase, followed by measuring the resulting $H_2O_2$. This purpose is served by using an electrode with a gold anode covered. with three membranes. A dialysis membrane permmeable to glucose, gases and inorganic ions but impermeable to larger molecules, such as proteins, functions as a selector Provided therebelow is an enzyme membrane functioning as a kind of reaction space. Contained therein is the immobilized enzyme glucose oxidase. A sealing lipophilic membrane with incorporated proton carrier molecules is closest to the gold anode. The glucose diffusing through the dialysis membrane reacts in the presence of the enzyme with oxygen, thus forming $H_2O_2$. The $H_2O_2$ is oxidized at the gold anode so as to form 2 protons. These are eliminated by the proton carriers. With this sensor Kessler carried out measurements in the peritoneum of anesthetized rats. He found a good correlation between the glucose values measured in the peritoneum and the real blood glucose values. Dimensions of the electrode are not mentioned, but an electrode suitable for implantation in human beings is not yet available.

A. Müller and P. Abel of the Zentralinstitut für Diabetes "Gerhardt Katsch" from Karlsberg (GDR) also have a glucose oxidase/$H_2O_2$ sensor available [Biomed. Biochim. Acta 43 (1984) 577-584; Biomed. Biochim. Acta 45 (1986) 769-777]. Again the immobilized enzyme is fixed to the electrode (Pt) surface This is spanned by respectively a hydrophobic and a hydrophilic membrane as a selector for the glucose. After a starting period of 24 hours this electrode gives a stable signal, i.e. a current of 0.02-6.8 nA, according to the glucose concentration. It is 7 cm in length and has a diameter of 2-4 mm. The electrode was implanted in 6 dogs and the glucose was measured. The ratio between glucose concentrations in blood and in tissue then varies from 33 to 70%. Besides this large spreading, failures occur frequently so that a good in vivo calibration is not possible.

All the glucose sensors hitherto developed rhat have already reached the experimental in vivo stage are therefore based on a system with immobilized enzyme glucose oxidase. This has the advantage that the electrode can be miniaturized and readily implanted in whole. However, an important drawback is that under those conditions the enzyme is stable for a very short time only and that consequently frequent replacement (3-4 days) of the electrode is necessary. Another requirement in the technique of immobilization is that each electrode must be calibrated individually and that it takes a day before the electrode can give a stable signal.

In EP-A 0 134 758 Bombardieri also describes a glucose sensor starting from the same principle as the above discussed sensors: the selector is a membrane on which the enzyme glucose oxidase is immobilized. However, he does not provide the glucose sensor subcutaneously as the other authors do, but he connects the sensor to a perfusion system which uses long and/or many hollow fibers inserted into subcutaneous tissue to transport low-molecular substances, inter alia glucose, in the same concentratations as prevailing subcutaneously from said tissue to a place outside the body. The advantage of this method is that the membrane with immobilized enzyme can be easily replaced without requiring anything to be done subcutaneously. The drawback of this method as compared with, e.g., the Shichiri electrode is that the extensive hollow fiber package is to be applied surgically by making an incision in the skin. Since inflammation reactions inevitably occur in the place where the perfusion system penetrates the skin, the hollow fibers package has to be displaced at least every two weeks, which involves new surgery. Consequently, the practical usability of his system as a wearable sensor for continuous determination of glucose is very limited.

The object of the invention is to provide a wearable glucose sensor avoiding these drawbacks and particularly capable of being easily applied by the user himself and continuously giving reliable measuring results on the basis of which the administration of medicines, such as insulin, in response to the actually prevailing glucose concentration can be regulated without requiring frequent replacements of component parts, especially of parts applied under the skin.

This object is achieved according to the invention by a process of the type defined in the opening paragraph, which is characterized in that a perfusion fluid which contains dissolved glucose oxidase, or in which glucose oxidase is dissolved before reaching the measuring cell, is passed continuously or intermittently at a constant rate via a supply tube through a hollow fiber provided in the subcutaneous tissue and permeable to glucose and is passed via an airtight discharge tube from the hollow fiber to a measuring cell provided outside the body, with a dialysis taking place subcutaneously whereby glucose passes via the wall of the hollow fiber from the tissue into the perfusion fluid in an amount proportional to the locally prevailing glucose concentration, and with the glucose received in the perfusion fluid being completely oxidized before reaching the measuring cell.

In this connection it is preferred according to the invention that the used amount of oxygen is measured and that a measuring cell is used which comprises an operating electrode, an electrolyte space filled with electrolyte and a reference electrode and the perfusion fluid is passed along the measuring cell via a flow chamber provided in a flow element, said flow chamber having an inlet for the perfusion fluid discharged from the hollow fiber and an outlet for the perfusion fluid and being separated from the measuring cell by a membrane permeable to oxygen gas. As regards the measuring cell, it is preferred that an operating electrode of a noble metal, such as gold, silver and preferably platinum, and a reference electrode of silver are used, the electrolyte employed is a potassium phosphate buffer, preferably 0.5M $K_2HPO_4$, the employed membrane permeable to oxygen gas is a hydrophobic membrane, preferably a Polytetrafluorethylene membrane, and a voltage negative with respect to the reference electrode of about 0.6 V is applied to the operating electrode.

As every biosensor the new wearable glucose sensor according to the invention consists of a "selector" portion and a "detector" portion.

The selector portion, namely, the perfusion system, ensures that only glucose is measured from the plurality of substances circulating in the body; then the amount is determined by means of the detector, namely, the measuring cell.

For the selector two membranes and the enzyme glucose oxidase(GOD) are used, and the detector employed is an electrode giving an electric signal.

The principle of the glucose sensor is known and is based on the following reaction:

$$\text{glucose} + O_2 \xrightarrow{\text{GOD}} \text{glucono-}\delta\text{-lactone} + H_2O_2$$

The electrode measures the amount of $O_2$ remaining from the reaction or the resultant amount of $H_2O_2$ depending on the voltage applied to the electrode.

The selector employed by the glucose sensor according to the invention is a perfusion system which includes a subcutaneous dialysis step in which glucose diffuses from the subcutaneous tissue through the wall of the hollow fiber into the dialysis fluid in which the reaction catalyzed by the enzyme between glucose and oxygen takes place. This subcutaneous dialysis step is absent in the known glucose sensors, except for that of Bombardieri. With Bombardieri, however, the reaction step by means of non-immobilized enzyme in the perfusion systemis absent.

The dialysis step is deemed necessary for a reliable glucose sensor on an enzymatic basis for the following reasons:

(1) The $O_2$ concentration (saturated in water or body fluid) is not sufficient to completely convert physiological glucose concentrations by means of the enzyme. At glucose concentrations of 100 mg/dl or more the $O_2$ concentration is already zero and glucose is no longer measurable. Therefore, the glucose concentration must be diluted with respect to the $O_2$ concentration in the measuring fluid. This is only achieved by the subcutaneous dialysis system according to the invention in which a short hollow fiber is used. The use of a short hollow fiber according to the invention has the additional advantage that it can be easily applied by the user himself by means of a needle.

(2) The enzyme GOD has a high breakdown rate at 37° C. and continuous measurement. It is therefore necessary to use new enzyme every day or every two days. This can be easily done by means of the dialysis system according to the invention without requiring replacement of component parts applied under the skin.

In various modifications of the invention there can be used, e.g., an enzyme metering device located outside the body which ensures automatic supply of solid enzyme to the perfusion fluid in which enzyme is to be dissolved. Thus the breakdown problem is easily avoided and a long service life can be realized without intermediate enzyme replacement of, e.g., at least two and a half months. In other modifications of the invention there is used a reservoir filled with perfusion fluid, which is located outside the body and can be easily replaced by a new reservoir filled with perfusion fluid.

As stated before, the used amount of oxygen is preferably measured according to the invention. This has the advantage that less stringent requirements need to be imposed on the quality of the employed enzyme. If the glucose sensor would be based on a measurement of the resultant amount of hydrogen peroxide, traces of the enzyme catalase which catalyzes the breakdown of hydrogen peroxide could adversely affect the accuracy of the measurement. However, when the used amount of oxygen is measured, the presence of catalase is favorable and some modifications of the invention therefore use a perfusion fluid containing both glucose oxidase and catalase. A second problem associated with a measurement of the resultant amount of hydrogen peroxide is that the dialysis fluid containing the $H_2O_2$ formed is to be immediately contacted with the electrode resulting in that other substances in the dialysis fluid may have a disturbing effect on the measurement. This last-mentioned drawback may perhaps be removed by using special membranes, e.g., specific cellulose ester membranes, but a perfect separation of dialysis fluid and electrode which only allows hydrogen peroxide to pass is hard to realize. If, however, the used amount of oxygen is measured, the dialysis fluid can be perfectly kept separated from the electrode by means of a membrane which is only permeable to gases, such as a Teflon membrane, and the measurement can be carried out in a well defined electrolyte, such as a potassium phosphate buffer of 0.5M $K_2HPO_4$.

A number of modifications of the process according to the invention is characterized in that the perfusion fluid is supplied through an airtight supply tube, preferably of polyethylene, or through an air-permeable supply tube, preferably of Teflon or silicone rubber, from a reservoir provided outside the body and is discharged after passing through the measuring cell to a receptacle likewise provided outside the body.

Such a process can be carried out, e.g., in such a manner that the employed perfusion fluid supplied from the reservoir is a physiological saline solution which is contacted outside the body with glucose oxidase after passing through the hollow fiber and before passing through the measuring cell.

Such a process, however, is preferably carried out in such a manner that the employed perfusion fluid supplied from the reservoir is a solution of glucose oxidase in a physiological saline solution. It is then preferred that the perfusion fluid contains at least 0.05 mg, preferably at least 0.10 mg glucose oxidase per ml physiological saline solution, and preferably 0.20-0.40 mg glucose oxidase per ml. The flow rate of the perfusion fluid will preferably be 0.1-1.0 ml/hour, and most preferably 0.2-0.4 ml/hour.

A much preferred modification of the process according to the invention in which a circulation of perfusion fluid is used is characterized in that the perfusion fluid employed is a physiological saline solution containing the enzymes glucose oxidase and catalase in the dissolved state, the perfusion fluid is returned after passing through the measuring cell to the hollow fiber via a system comprising at least one air-permeable part, and before or after passing through the measuring cell the perfusion fluid is passed through an enzyme metering device provided outside the body, in which device a new amount of glucose oxidase and catalase is dissolved in the perfusion fluid.

It is then preferred that after passing through the measuring cell the perfusion fluid is returned to the hollow fiber via an air-permeable supply tube, preferably of Teflon or silicone rubber. It is further preferred that the perfusion fluid contains at least 0.05 mg, preferably at least 0.10 mg glucose oxidase and at least 0.05 mg, preferably at least 0.10 mg catalase per ml physiological saline solution, and most preferably oxidase and 0.20-0.40 mg catalase per ml.

The hollow fiber required for the dialysis step must pass glucose. It is preferred that a hollow fiber of cellulose ester (such as cellulose acetate) having a molecular weight cut off value of about 10 kD is used. However, other types of materials are also useful, such as hollow fibers of polysulfone or acrylic copolymer (Amicon). The preferred cellulose fiber, however, is stronger and more flexible and can be inserted into the body more easily than the thicker and more vulnerable Amicon fiber.

As regards sizes, it is preferred that a hollow fiber is used having an inner diameter of 100-500 $\mu$m, preferably 120-200 $\mu$m, an outer diameter of 130-550 $\mu$m, preferably 150-250 $\mu$m, and is 0.1-3 cm, preferably 0.5-2.5 cm, in length. Also, the nature of the supply and discharge tubes is not critical, provided, anyhow, the discharge tube is airtight. Polyethylene tubes are preferred in the case of airtight tubes and a Teflon or silicone rubber tube in the case of an air-permeable supply tube. As for their sizes, it is preferred that the supply and discharge tubes have an inner diameter of 0.2-0.6 mm, preferably 0.25-0.35 mm, and an outer diameter of 0.4-1.0 mm, preferably 0.6-0.8 mm.

The length of the airtight discharge tube between the hollow fiber and the flow chamber must preferably be as short as possible, so as to enable a rapid response. It is preferred that the airtight discharge tube between the hollow fiber and the flow chamber is 1-10 cm, preferably 1-5 cm, in length.

As regards the flow element, it is preferred in connection with a high accuracy of the glucose sensor that a flow chamber is used having such sizes, shape and position of the perfusion fluid inlet and outlet that substantially no dead spaces occur. The exposed surface of the operating electrode which is separated from the perfusion fluid by the membrane permeable to oxygen (or to $H_2O_2$) may be transverse to the direction of flow the perfusion fluid or may also be in line with the perfusion fluid inlet opening, the distance between the inlet opening and the exposed surface of the operating electrode being preferably less than 5 mm, and most preferably less than 1 mm.

The nature of the reservoir for perfusion fluid, if used, is not critical, on condition that it has a drive mechanism (pump) with which the perfusion fluid contained therein can be pressed through the supply tube connected thereto at a constant rate. The receptacle employed is preferably a plastic bag.

In some modifications use is made of an enzyme metering device. By this is generally meant a system capable of keeping the concentration of enzymes (glucose oxidase and catalase) constant in the glucose sensor with a fully closed circuit, the object of which is to enable reliable continuous measurements of the subcutaneous glucose level without replacements at the sensor, for a longer period of time.

While in case of an open-circuit sensor the reservoir with enzyme-containing perfusion fluid must be replaced by the user every two days, the enzyme metering device can automatically adopt this task in the closed-circuit sensor, and as in physiological processes, said device can supplement the amount of enzymes broken down.

Different modifications of an enzyme metering system are conceivable:

(a) Slow-release tablets:

The enzymes (glucose oxidase and catalase) can be tabletted together with noninterfering adjuvants suitable therefor, the tablets releasing the active ingredients (in the presence case the enzymes) slowly to the solvent.

Tablets having different release profiles already exist and can be adapted for the release of enzymes By introducing a suitable enzyme-release tablet into a reservoir from which the perfusion fluid is circulated, the concentration of enzymes can be kept intact for a long period of time. Even a mechanical system is conceivable which releases a new tablet in the reservoir at given times.

(b) Hollow fiber system:

The enzyme release to the perfusion system, can also be effected with a hollow fiber. The molecular weight of glucose oxidase is 119,000; by selecting a hollow fiber having a molecular weight cut off of about 100,000, it is possible to have the enzyme diffuse slowly therethrough. The enzyme is then contained in solid form in an enclosed space outside the hollow fiber, and the perfusion fluid flows through the hollow fiber. The molecular weight cut off and the length of the fiber determine the amount of enzyme released to the perfusion system per unit of time.

After optimization of these parameters there is formed a passive release system which can keep the concentration of the enzyme constant.

Also in the case of the closed system (perfusion fluid circulation) there can be used a reservoir for perfusion fluid. The reservoir and the enzyme metering device are preferably combined in one component part. ied in a system The invention is further embodied in a system for continuously or intermittently determining the glucose concentration in subcutaneous tissue, characterized by a hollow fiber permeable to glucose a supply tube for perfusion fluid;

an airtight discharge tube for perfusion fluid; and a measuring cell for measuring the amount of oxygen or the amount of hydrogen peroxide in the perfusion fluid.

Such a system can further be characterized by a reservoir for perfusion fluid provided with a device for passing perfusion fluid contained in the reservoir through the hollow fiber at a constant rate via the supply tube connected to the reservoir; a receptacle for employed perfusion fluid; and, if desired, a perfusion fluid contained in the reservoir, said fluid consisting of a solution of glucose oxidase in a physiological saline solution; or can further be characterized by an air-permeable supply tube for perfusion fluid; an enzyme metering device; a pump for circulating perfusion fluid at a constant rate; if desired, a supply contained in the enzyme metering device of the enzymes glucose oxidase and catalase in solid form; and, if desired, an amount of perfusion fluid consisting of a solution of the enzymes glucose oxidase and catalase in a physiological saline solution.

The invention is also embodied in a measuring cell assembly suitable for use in this system, which is characterized by a measuring cell comprising an operating electrode, an electrolyte space and a reference electrode, as well as a pertaining flow element for perfusion fluid comprising an inlet and an outlet for perfusion fluid which communicate with a flow chamber capable of being separated from the measuring cell by an oxygen gas-permeable membrane.

The invention is further embodied in an assembly for continuously or intermittently regulating the glucose content in blood, which is characterized by a system for continuously or intermittently determining the glucose concentration in subcutaneous tissue as defined above, as well as a regulable injection system for introducing medicines, such as insulin, into the blood; and a calculating and regulating system for calculating the glucose concentration in the subcutaneous tissue on the basis of the measuring values of the measuring cell and a pertaining calibration curve, by means of an algorithm, the characteristic and relevant parameters of which are contained in a mathematical model, determining the amount of medicine to be supplied and controlling the regulable injection system in such a manner that the glucose concentration in the tissue and/or in the blood remains within predetermined values. Preferably, the calculating unit also has alarm function in case of extreme glucose concentrations in the body and in case of failures. The calculating unit can also have the secondary task of monitoring the curve of the memory concentration and insulin supply, storing same in the local memory and transporting same upon command of an external system to other data processing systems.

In the following the invention will be explained with reference to the accompanying drawings and by means of a description of conducted experiments.

Figure 1:
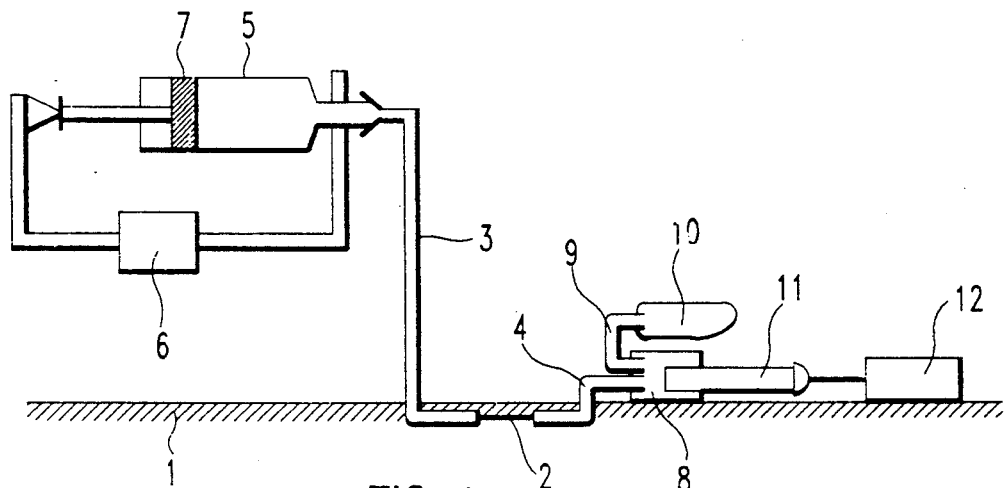
FIG. 1 is diagrammatic cross-sectional view of a wearable glucose sensor according to the invention.

As diagrammatically shown in FIG. 1, the system according to the invention for continuously determining the glucose concentration in subcutaneous tissue comprises a hollow fiber (2) to be applied under the skin (1), said hollow fiber being connected via an airtight supply tube (3) and an airtight discharge tube (4) to component parts located outside the body. The supply tube (3) can be connected to a reservoir (5) for perfusion fluid, a device (7) driven by a pump (6) being provided to force the perfusion fluid contained in the reservoir through the hollow fiber at a constant rate via the supply tube. The supply tube (4) can be connected to the perfusion fluid inlet of a flow element (8), the perfusion fluid outlet of which is connected via a tube (9) to a receptable (10) for employed perfusion fluid. Connected to the flow element (8) is a measuring cell (11) also referred to as electrode, said measuring cell being connected to a potentiostat (12).

Of course, modifications other than those shown in FIG. 1 are possible too. Thus, for instance, it is not necessary that the supply tube and the discharge tube pass through the skin in different places and that the hollow fiber extends in one direction only. When a looped hollow fiber is used, one hole in the skin will suffice for supply and discharge purposes, glued joints in the body can be avoided and stresses, if any, on the follow fiber caused by a moving person can be avoided too.

Figure 2:
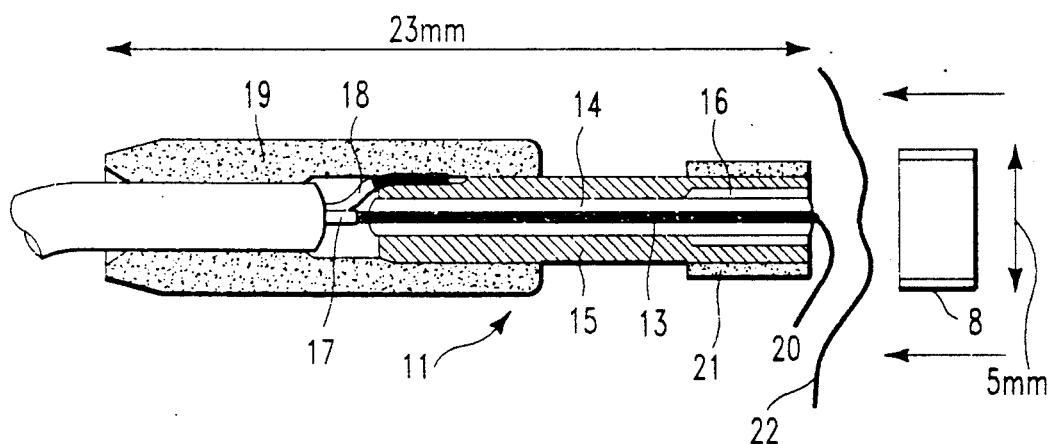
FIG. 2 is a diagrammatic cross-sectional view of a measuring cell assembly according to the invention.

As diagrammatically shown in FIG. 2, the measuring cell (11) comprises an operating electrode (13) separated by an isolating jacket (14) of, e.g., glass or plastic from a reference electrode (15) adhered to the isolating jacket (14), e.g., by means of an epoxy resin. The operating electrode preferably consists of a platinum wire, the operating surface of which is limited to the tip. The reference electrode preferably consists of a silver sleeve in which an electrode space (16) is milled out. The operating electrode and reference electrode are connected via jacketed current conductors (17) and (18),respectively, to a potentiostat (not shown in FIG. 2). The reference electrode is enclosed within an isolating jacket (19) of, e.g., glass or plastic. As shown in FIG. 2, it is not necessary to jacket the entire outer surface of the reference electrode. At the end of the measuring cell where the exposed operating surface (20) of the operating electrode and the electrolyte space (16) are provided the reference electrode is enclosed within an isolating jacket (21) which is preferably made of glass or a hard plastic, and the outer diameter of which is adapted to the sizes of the flow element (8) (only diagrammatically shown in FIG. 2) in such a manner that the flow element can be pushed fittingly over this isolating jacket (21). The membrane permeable to oxygen gas and impermeable to fluid or the membrane permeable to $H_2O_2$ which separates the flow chamber for perfusion fluid, as provided within the flow element, from the measuring cell may consist in a preferred embodiment of a separate sheet (22) of, e.g., Teflon in the case of an oxygen electrode which is enclosed between the jacket (21) and the flow element (8) when the flow element advances on the measuring cell. The operating electrode, the reference electrode and the electrolyte space filled with an electrolyte are thereby separated from the space in the flow element referred to as flow chamber, through which the perfusion fluid from the hollow fiber is passed. The membrane, however, may also be a fixed part of the measuring cell or may be applied by dip techniques. In the case of the oxygen electrode any hydrophobic membrane that only passes gases is suitable. Indicated in FIG. 2 are further the most important sizes of the miniature measuring cell employed in the experiments, namely a length of about 23 mm and a diameter in the order of magnitude of 5 mm.

Figure 3:
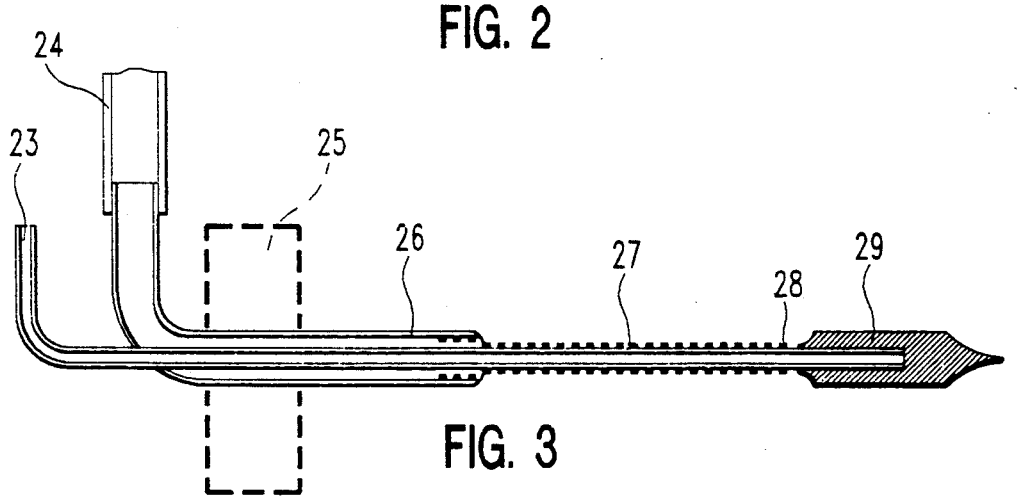
FIG. 3 is a diagrammatic cross-sectional view of a hollow fiber of polyacrylate mounted on a needle.

The system according to the invention may comprise a hollow fiber having a diameter of 500-1200 μm, preferably 900-1100 μm, such as an Amicon hollow fiber, which, mounted on a needle as shown in FIG. 3, can be directly inserted under the skin. The hollow fiber-on-needle shown in FIG. 3 comprises a supply tube (23), a discharged tube (24), a silicone butterfly (25), a double-lumen outer tube (26), a polysulfone hollow fiber (27), a perfusion fluid turning point (28) and a needle point (29).

Preference, however, is given to hollow fibers of cellulose ester having an external diameter of 150-250 μm, which are preferably used as follows. First of all the hollow fiber is to be positioned. To achieve this, according to a first method a hypodermic needle (1.20×40 mm) is inserted through the skin into the subcutaneous fat tissue preferably somewhere on the abdomen (few pain receptors), followed by passing the tip of the needle through the skin again from the inside to the outside. Thus, a guide tube is formed through which the tubing consisting of supply tube (3), hollow fiber (2) and discharge tube (4) is drawn until the hollow fiber is in the needle (the supply and discharge tubes, for instance, are firmly fixed to the hollow fiber with glue). Then the needle is withdrawn so that only the hollow fiber with a small part of the supply and discharge tubes remains in the body. Subsequently, the other component parts are connected thereto outside the body. According to a second method a catheter containing a needle is passed through the skin into the subcutaneous fat tissue, followed by withdrawal of the needle. A looped hollow fiber is introduced into the catheter positioned, followed by pushing back the catheter so far that the looped hollow fiber remains in the subcutaneous tissue in exposed condition.

In order to make it possible to carry out the subcutaneous dialysis at a constant rate of preferably 0.3 ml/hour, perfusion fluid is passed through the hollow fiber via the supply tube. The perfusion fluid contained in the reservoir (5) is preferably a solution of the enzyme glucose oxidase in a physiological saline solution, e.g., a solution containing 0.25 mg GOD per ml.

The glucose present in the subcutaneous fat tissue diffuses through the wall of the hollow fiber into the perfusion fluid in which the reaction between the glucose and the oxygen takes place with catalysis of the enzyme. Via the discharge tube (4) glued to the other side of the hollow fiber (2) the perfusion fluid is discharged to a miniaturized oxygen electrode located outside the body where the remaining amount of oxygen from the enzymatic reaction is determined and is converted into an electric signal. The dialysis fluid is then discharged to a bag (10). The electrode is connected via a jacketed 2-core cable to a potentiostat (12) which maintains a fixed voltage ($-0.6$ V) on the electrode and measures the current strength caused by the oxygen.

An alternative, which will not be discussed in more detail, is the use of a physiological saline solution as perfusion fluid in combination with a reaction space containing the enzyme,said space being provided outside the body between the discharge tube (4) and the oxygen electrode (11). By passing the perfusion fluid, which in the hollow fiber (2) has received glucose from the tissue, via the discharge tube (4) through this separate reaction space, it can likewise be ensured that the desired reaction takes place before the perfusion fluid reaches the oxygen electrode. Although this variant requires an additional component part, namely, an enzyme-containing separate reaction space, it could be advantageous, because the enzyme remains outside the body.

With the measuring cell specificity to oxygen is obtained by applying a negative voltage of 0.6 V to the operating electrode with respect to the reference electrode. Electrons of the operating electrode will then reduce the oxygen passing through the membrane. The current strength measured with the potentiostat is proportional to the oxygen concentration and is read on the ammeter. The potentiostat is preferably a portable device fed by batteries and provided with a digital output and an analog output (in the case of experiments for determination purposes).

Figure 4:
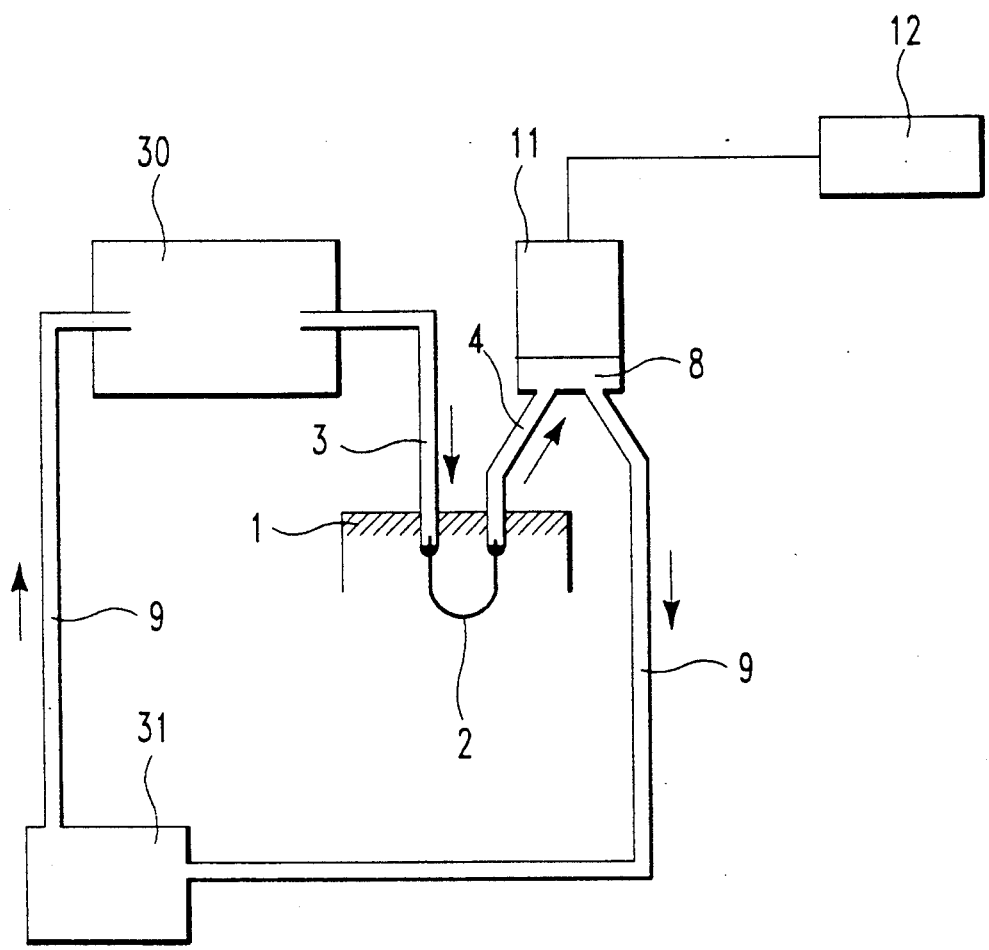
FIG. 4 is a diagrammatic representation of a wearable glucose sensor according to the invention in which a perfusion fluid circulation is used.

FIG. 4 shows a preferred embodiment of the invention in which the perfusion fluid is not conveyed from a reservoir to a receptacle, as in the embodiment of FIG. 1, but is circulated. Similar reference numerals refer to the component parts already discussed with respect to FIG. 1. A portable pump (30) provides the required circulation of the perfusion fluid. In order to enable a long service life, there is provided an enzyme metering device (31) which automatically releases a new amount of the enzymes glucose oxidase and catalase in solid form to and dissolves it in the passing perfusion fluid rate of 1.05 ml/hour. From the records of the recorder connected to the potentiostat the following parameters were derived:

| RESULTS: | | | | | | | |
|---|---|---|---|---|---|---|---|
| | Glucose 100 mg/dl: | | | | | | |
| | 1 | 2 | 3 | | | | aver. +/− S.D. |
| slope of sensor response (slope) | 7.5 | 7.4 | 8.7 | | | | 7.87 +/− 0.72 |
| deflection (parts) | 18.5 | 21.2 | 20.1 | | | | 19.93 +/− 1.36 |
| t 90% (sec.) | 156 | 192 | 144 | | | | 174 +/− 25 |
| | Glucose 200 mg/dl: | | | | | | |
| | 1 | 2 | 3 | 4 | | | aver. +/− S.D. |
| slope | 11.6 | 15.2 | 14.8 | 13.5 | | | 13.78 +/− 1.62 |
| deflection (parts) | 52.5 | 51.0 | 46.7 | 36.5 | | | 46.68 +/− 7.21 |
| t 90% (sec) | 228 | 180 | 192 | 144 | | | 186 +/− 35 |
| | Glucose 300 mg/dl: | | | | | | |
| | 1 | 2 | 3 | 4 | 5 | 6 | 7 | aver. +/− S.D. |
| slope | 18.2 | 19.0 | 18.0 | 23.0 | 22.4 | 18.6 | 20.2 | 19.9 +/− 2.40 |
| deflection | 59.5 | 61.8 | 68.4 | 57.8 | 60.2 | 64.3 | 65.0 | 62.3 +/− 3.68 |
| t 90% | 192 | 252 | 336 | 120 | 180 | 420 | 180 | 240 +/− 105 |
| | Glucose 400 mg/dl: | | | | | | |
| | 1 | 2 | 3 | | | | aver. +/− S.D. |
| slope | 21.8 | 24.3 | 26.6 | | | | 24.23 +/− 2.40 |
| deflection | 84.5 | 84.0 | 81.0 | | | | 83.17 +/− 1.89 |
| t 90% | 468 | 156 | 192 | | | | 272 +/− 171 | and can also provide deaeration, if so desired. Although the presence of catalase ensures that the aggressive hydrogen peroxide formed in the glucose oxidation is rapidly decomposed, it is inevitable that the enzyme activity decreases. By a continuous or regular replenishment with a fresh amount of enzyme it can be ensured that the enzyme activity in the perfusion fluid is permanently sufficient to rapidly and completely oxidize all of the absorbed glucose.

Because it is of course necessary that the perfusion fluid passed through the hollow fiber should always contain the same oxygen concentration, the employed oxygen is to be replenished somewhere after passing through the flow element (8) and before passing through the hollow fiber (2). For this purpose at least one air-permeable component part should be present in this part of the system, so that the perfusion fluid can absorb oxygen from the air until the saturation concentration has been reached. This can be realized in a very simple manner by means of an air-permeable supply tube (3) or by means of an air-permeable tube between the flow element (8) and the enzyme metering device (31) and/or between the device (31) and the pump (30).

In the experiments described below, unless otherwise mentioned, a tubing was used consisting of polyethylene supply and discharge tubes having an inner diameter of 0.29 mm and an outer diameter of 0.69 mm, and a hollow fiber of "saponified cellulose ester (SCE)" having a molecular weight cut off value (MWCO) of 10 kD, an inner diameter (in dry condition) of 150 μm ± 15 μm and an outer diameter (in dry condition) of about 186 μm. The discharge tube was about 1.5 cm in length.

IN VITRO EXPERIMENT

In this experiment the glucose sensor was tested by alternately suspending the hollow fiber which is 10 mm in length in vessels containing water or a glucose solution of a known concentration. An enzyme solution (GOD 0.15 mg/ml) was pumped through the fiber at a In all cases the response time (t res) was not more than 1 minute. The response time is the time lapsed between the moment of replacing the water by a glucose solution and the moment the recorder begins to deflect. By t 90% is meant the time lapsed between the former moment and the moment at which the deflection of the recorder reaches 90% of the plateau value. The slope of the sensor response indicates the rate at which the deflection increases.

Figure 5:
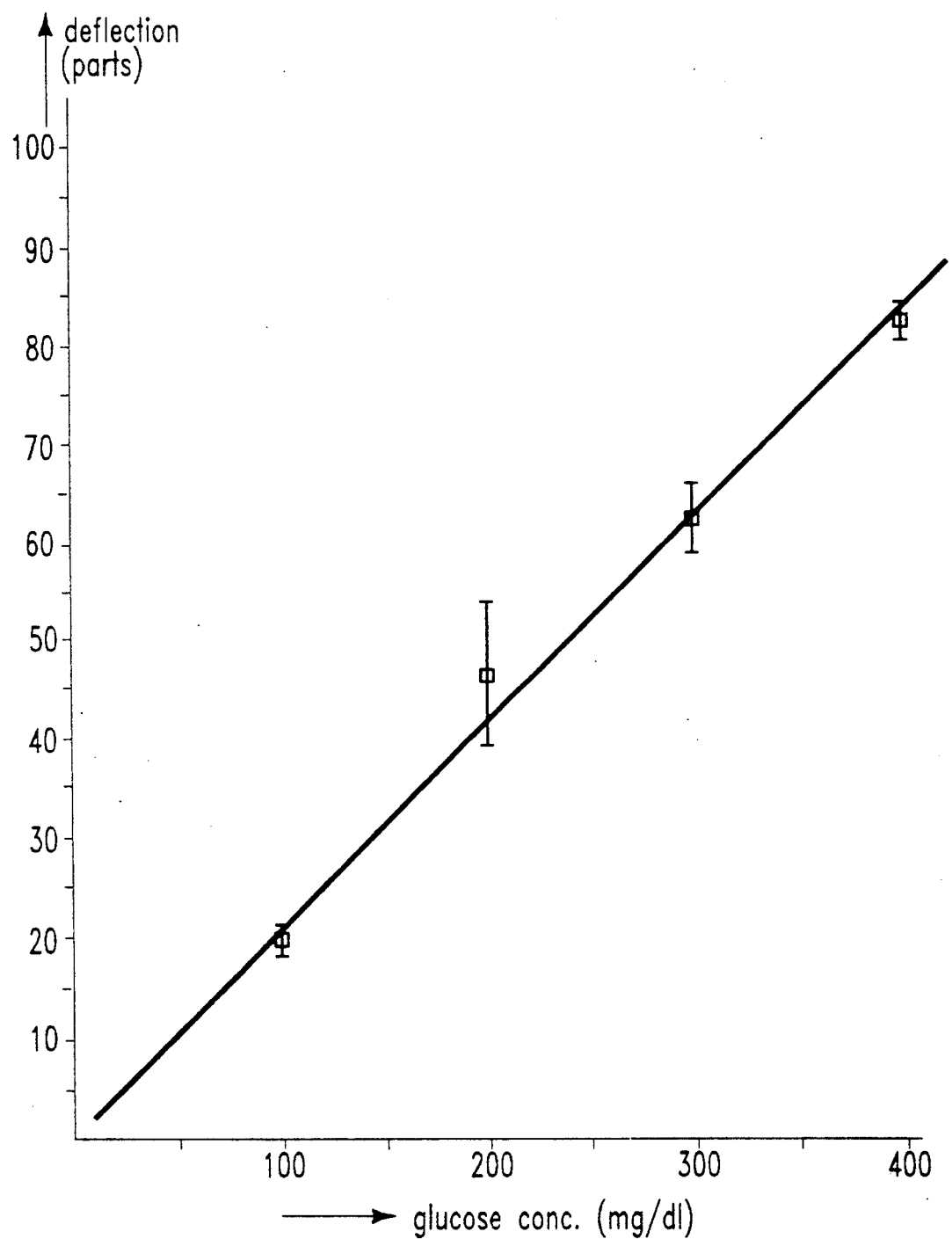
FIGS. 5–13 are graphically plotted results of in vitro and in vivo experiments.
Figure 6:
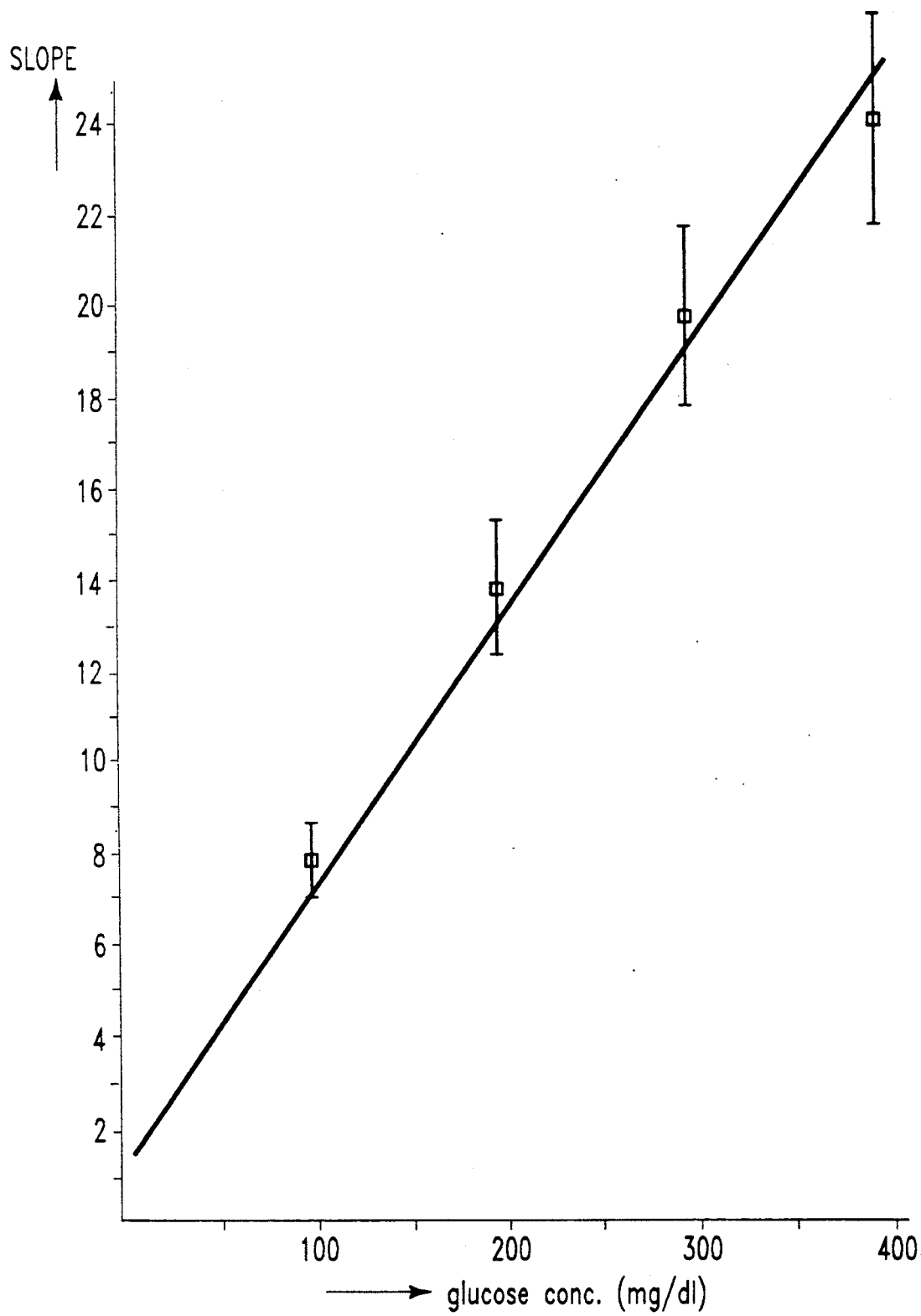

FIG. 5 shows the relation between the glucose concentration and the deflection on the recorder. FIG. 6 shows the relation between the glucose concentration and the slope and FIG. 7 the relation between the deflection and the slope.

As appears from FIG. 5, there is a linear relation between the concentration and the deflection. This means that the glucose sensor operates linearly in the concentration range of 0 to 400 mg/dl and that accordingly in this range the sensor signal is a measure of the glucose concentration.

Figure 7:
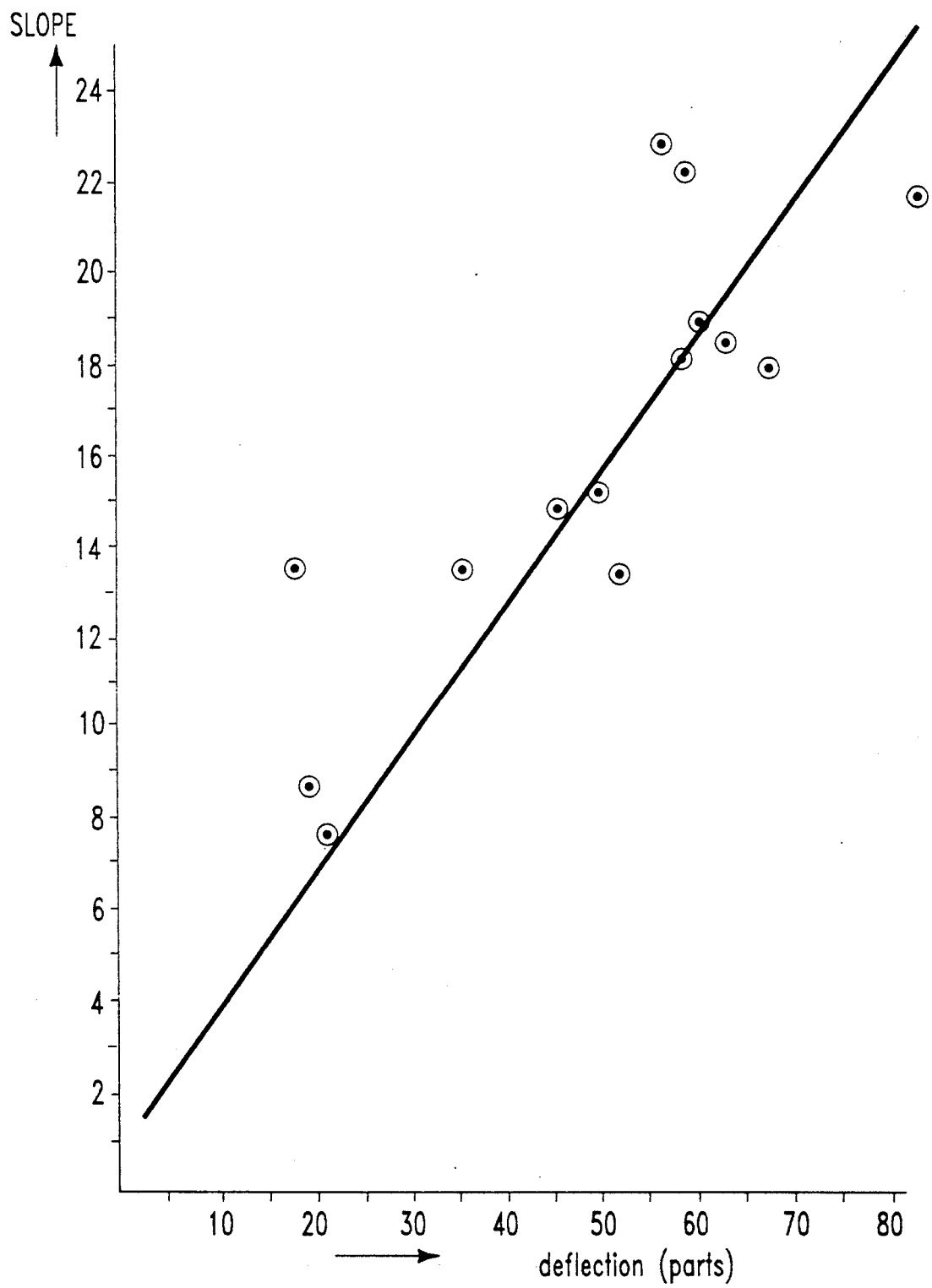

FIG. 6 shows that there is also a linear relation between the glucose concentration and the slope of the sensor response. The fact, however, is that at higher concentrations the determination of the slope becomes increasingly difficult, so that the standard deviation (SD) in question becomes greater and greater. In the case of in vivo measurements this plays no role because the glucose sensor is rapid enough so that the plateau values may be used to calculate the glucose concentration. FIG. 7 has shown that there is also a directly proportional relation between the deflection and the slope of an increase. This means that the slope is a proper measure of the level at which the plateau will adjust.

In the concentration range of 0 to 400 mg/dl the glucose sensor therefore gives a linear signal. This applies to both the slope and the plateau value.

IN VIVO EXPERIMENTS

(A) Long-Term Test on a Healthy Test Subject

Record:

On day 1 a hollow fiber (1.5 cm in length) is inserted into a healthy test subject. In order to study whether the sensor still functions well after some days in the body, measuring is started on day 6.

It concerns an open-circuit measurement, i.e. the perfusion fluid is collected and not returned to the hollow fiber.

Pump: peristaltic pump Minipuls II
Perfusion rate: 0.3 ml/hr
Enzyme concentration: 0.15 mg/ml After recording the basal glucose level for some time, glucose is orally administered to the test subject (t=0). The blood-sugar-level is monitored with the Yellow Springs, and the sensor continuously measures the glucose subcutaneously (FIGS. 8, 9 and 10).

day 6: 100 g glucose orally
day 7: 50 g glucose orally
day 9: 75 g glucose orally.

Figure 8:
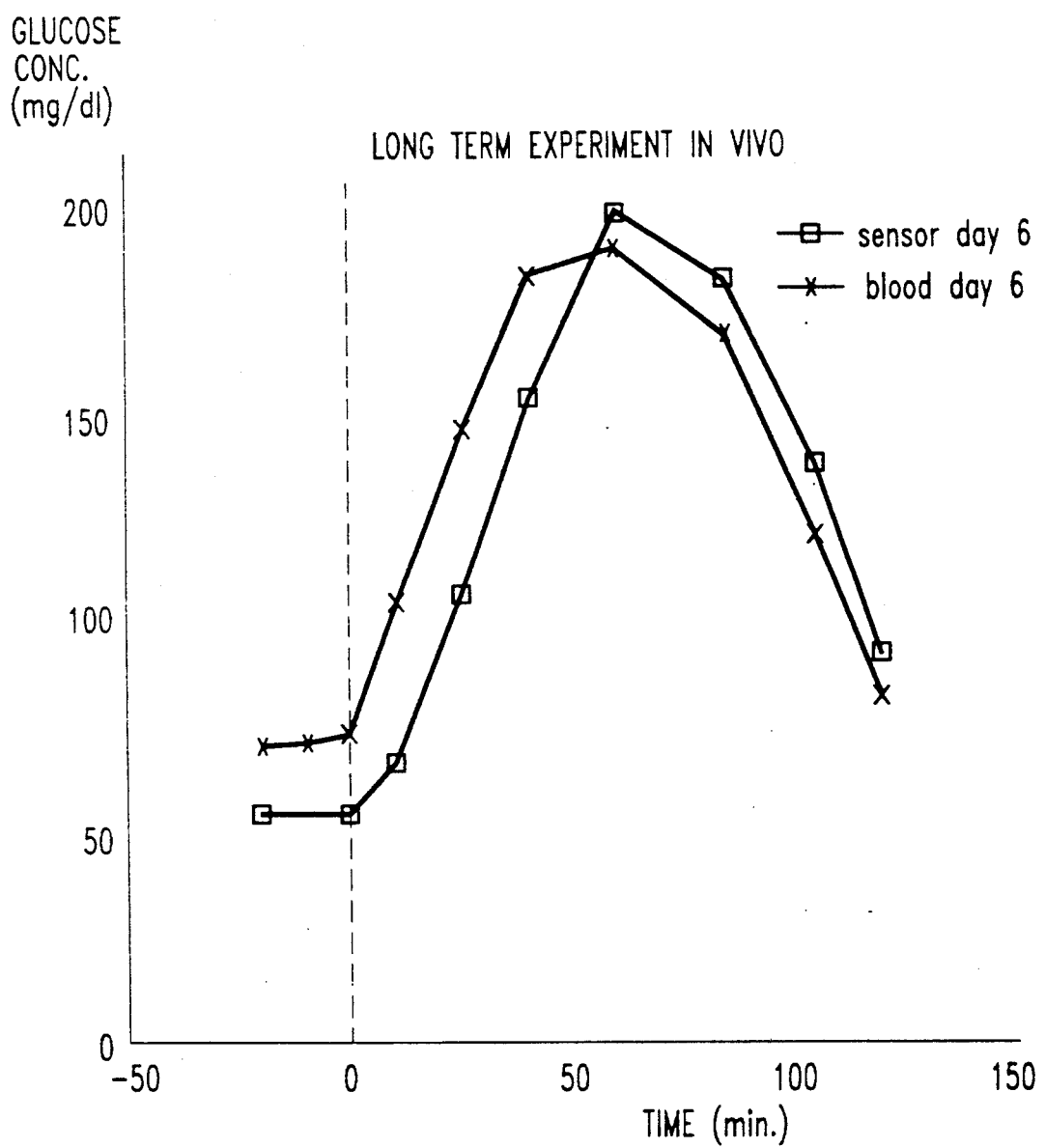
Figure 9:
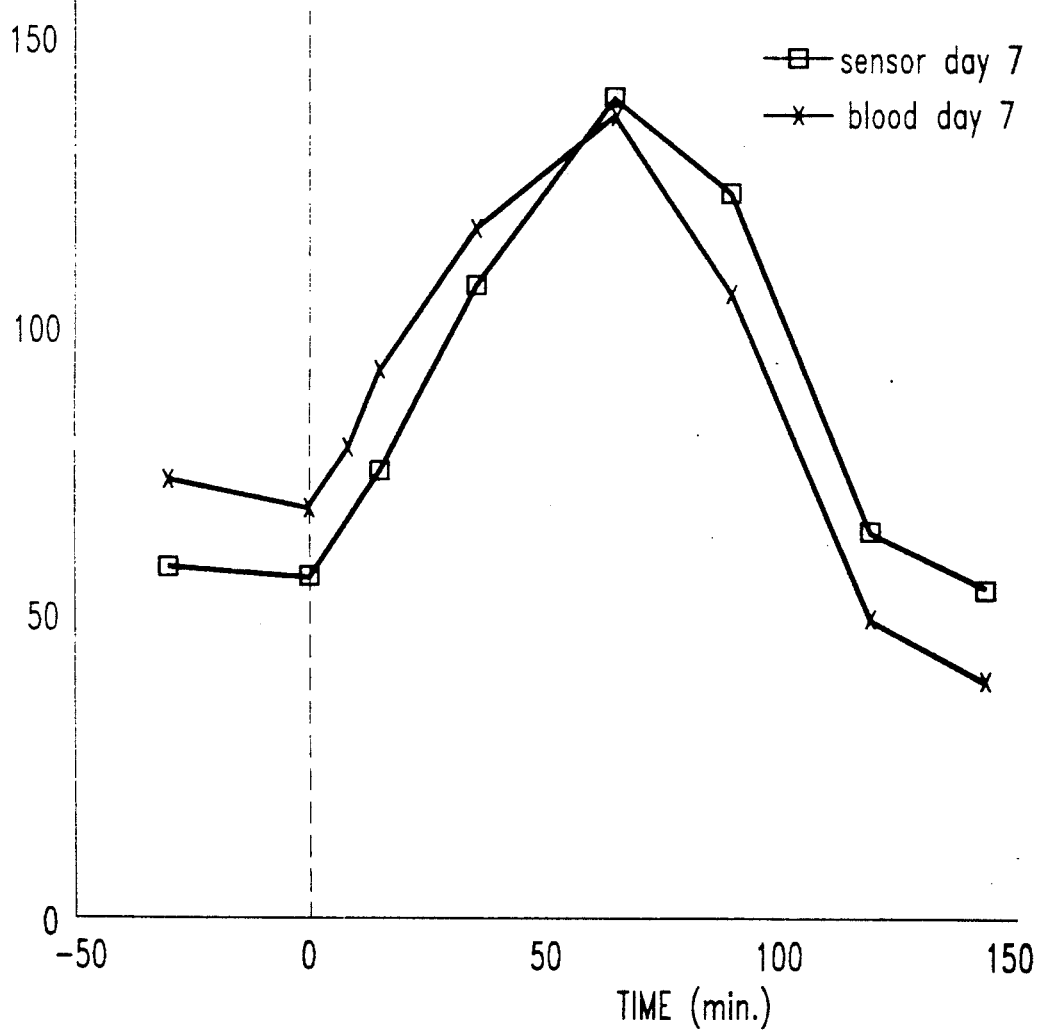
Figure 10:
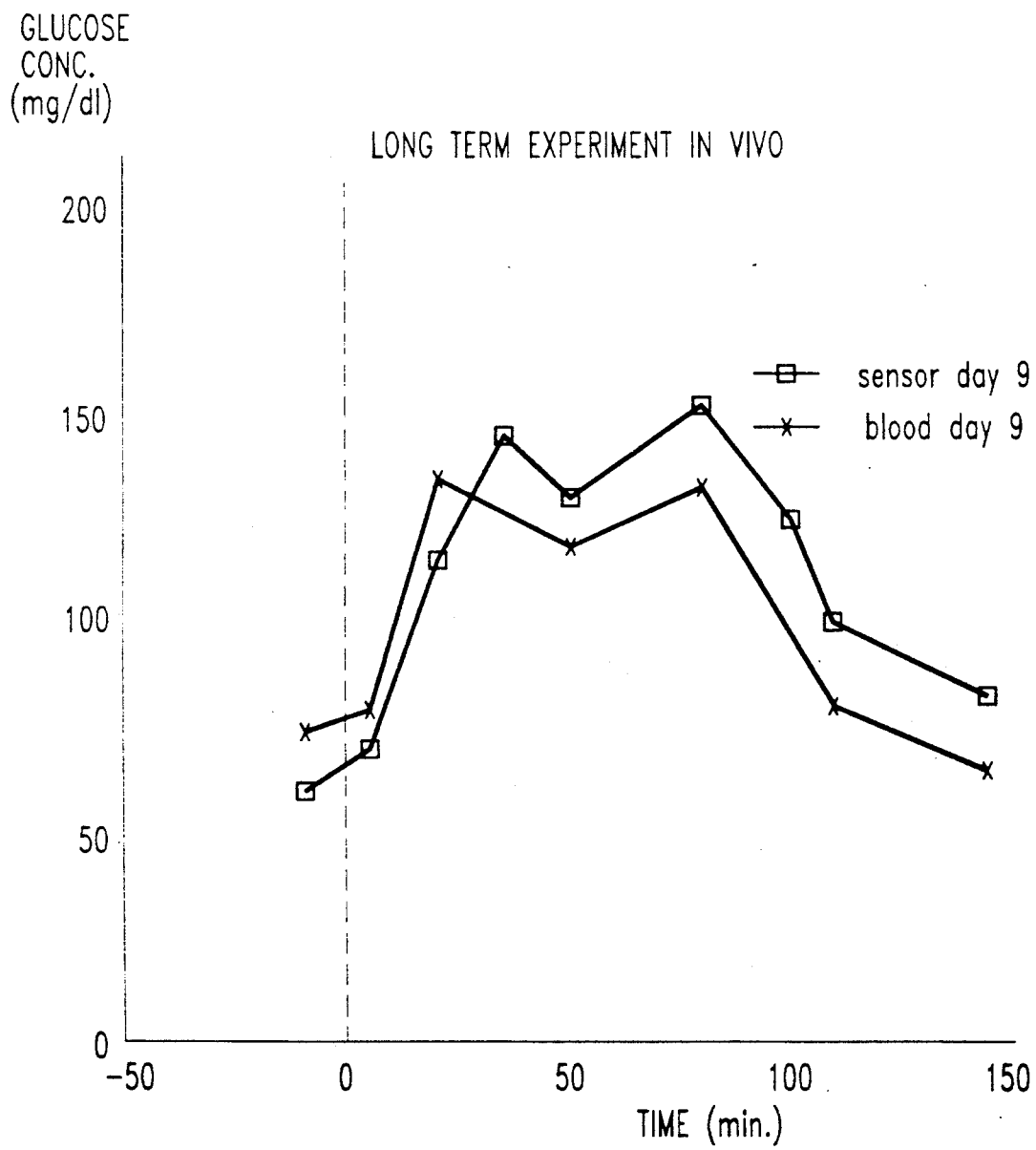

FIGS. 8, 9 and 10 show that the rise of the glucose level in the subcutaneous tissues occurs about 5 minutes later than the rise in the blood. The fall, too, starts about 5 minutes later. The glucose sensor itself has a response time of less than 1 minute, i.e. the delay observed is chiefly a physiological effect. It further appears that during the fall of the glucose levels the level is subcutaneously above the hematic level. An explanation of these observations resides in the fact that the insulin must first distribute over the bloodstream after which it inhibits the release of glucose by the liver This results in that the blood-sugar-level sinks. The insulin diffuses from the blood into the extracellular moisture after which it incites the cells to accelerate the absorption of glucose This explains why the fall in the subcutaneous tissues is later and faster than in the blood.

At the end of the test an equilibrium readjusts between the extracellular fluid (subcutaneously) and blood, so that the concentration is substantially equalized in both compartments.

Therefore, the glucose sensors seems to properly monitor the subcutaneous processes on all three days. The observations are physiologically explainable. Remarkable is the rather slight delay in the non-diabetic test subject between the changes in the blood and subcutaneously in comparison with diabetics (see the relevant places). This may indicate individual differences, but could also be based on the fact that the differences between intravascular and extravascular glucose concentrations in the physiological range during a non-steady state are much smaller than in disordered diabetics showing hyperglycemia.

After the experiment on day 9 the hollow fiber is easily removed from the body in undamaged condition. A small red irritated spot on the abdomen is the only thing that marks the place of insertion.

(B) Correlation Plot of Pilot Study on Healthy Test Subjects

Record:

100 g glucose is orally administered to 6 healthy test subjects on two successive days. During this oral glucose tolerance test the blood-sugar-level is measured, and furthermore the subcutaneous glucose concentration is monitored with the glucose sensor. The reservoir with enzyme is still a 10 ml syringe here which is exhausted by a pump (Braun VI). The perfusate is collected so that the circuit is not closed.

Perfusion rate: 0.3 ml/hr
Enzyme concentration: 0.15 mg/ml
Fiber length: 15 mm

Figure 11:
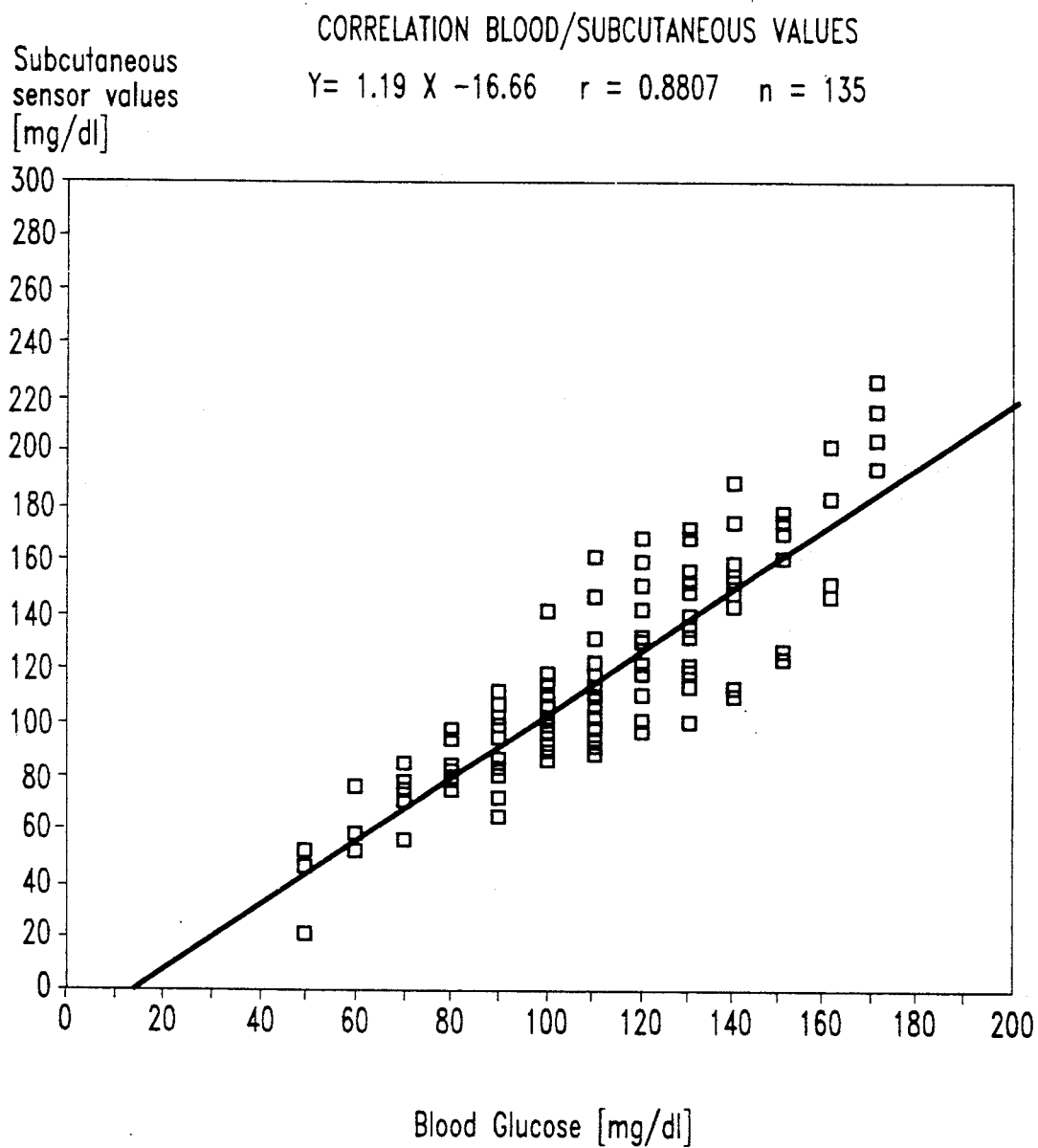

The subcutaneous and the blood sugar values of the rising as well as the sinking parts of the curves are all plotted together (FIG. 11). The resulting diagram shows the correlation between blood and sensor values (r=0.8807, n=135). The spreading between the different points is also an indication of the physiological delay between both compartments for which no correction is made here.

(C) Pilot Study on Diabetics

Record:

The patients take breakfast in the morning, but do not inject insulin so that the tests are started with a high blood-sugar-level. After recording the subcutaneous sugar level with the glucose sensor (check by means of blood sugars with the Yellow Springs) t=0 insulin is administered after which the fall of the glucose level is monitored.

A totally closed circuit is used in these experiments in which the perfusion fluid is returned to the reservoir (plastic vessel) for repeated use. The discharge tube is connected to the reservoir with an air-permeable tube (Teflon) in order to reinstate the oxygen concentration of the perfusion fluid. Catalase is also added to the perfusion fluid in order to remove the hydrogen peroxide formed.

Perfusion rate: 0.3–1.2 ml/hr
Fiber length: 15 mm
Enzyme concentration: 0.3 mg/ml (GOD and catalase)

Figure 12:
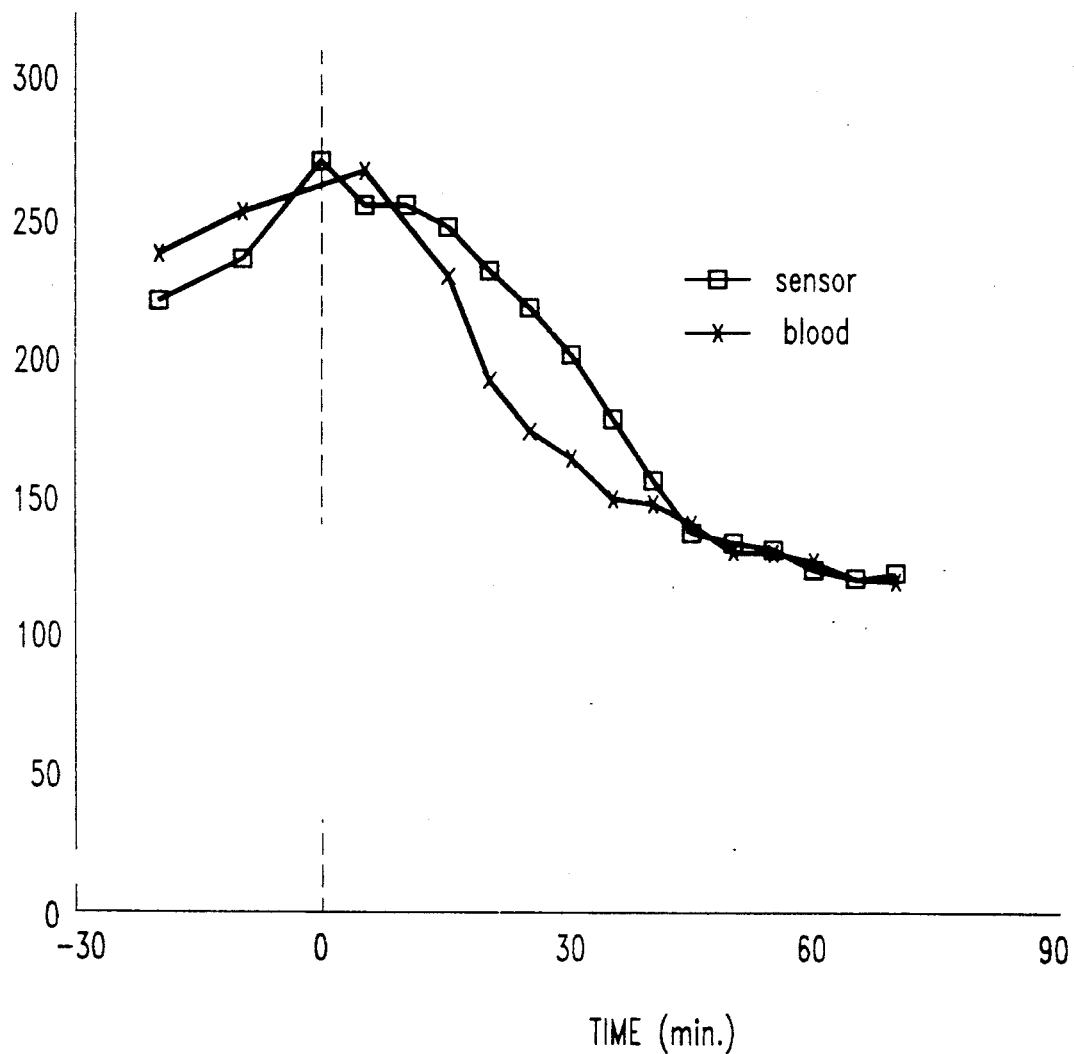

An example of such a recording is FIG. 12 in which the fall is clearly visible as well as the physiological delay ensuring that the sensor signal will fall somewhat later. This physiological delay differs from 5 to 20 minutes among the 11 diabetics.

Figure 13:
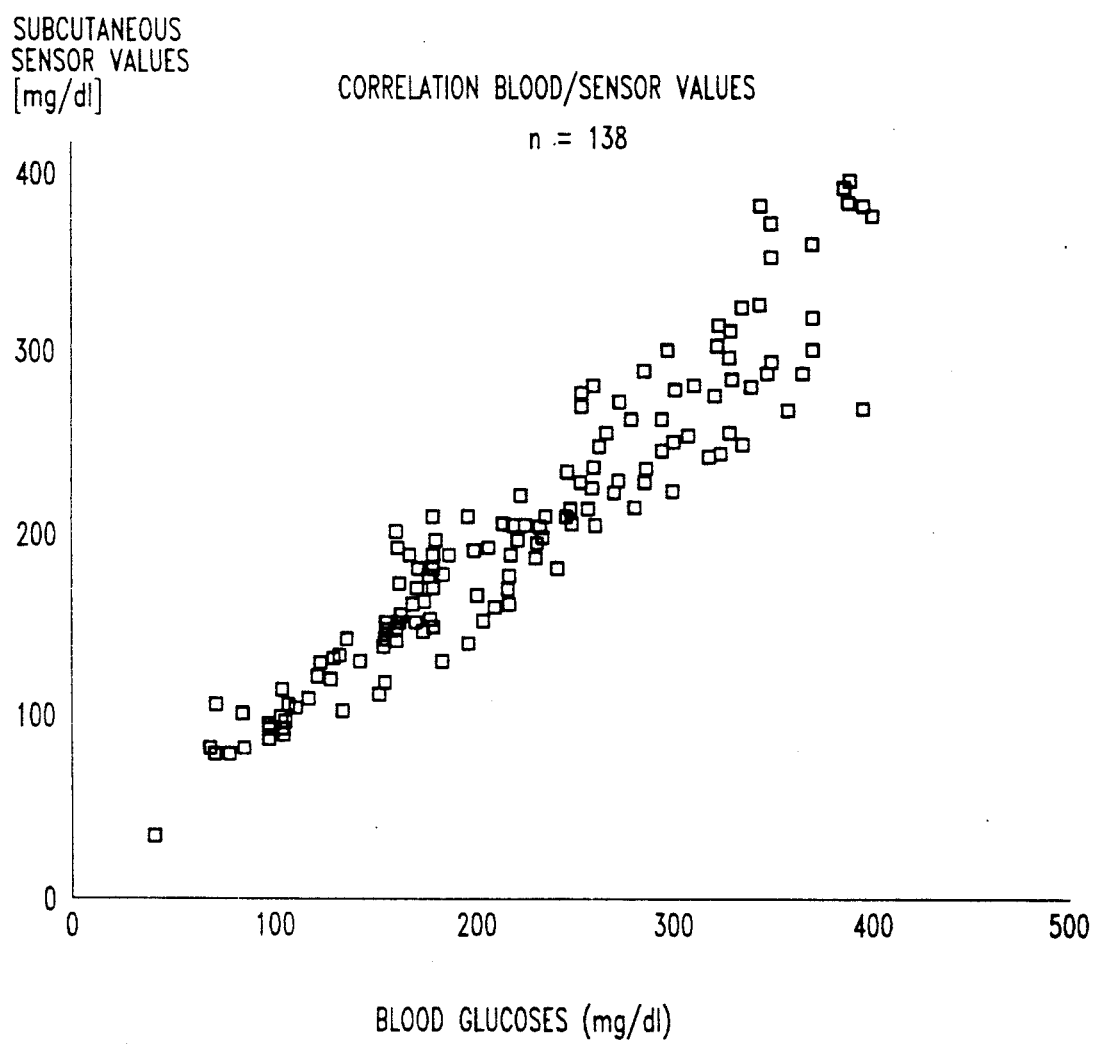

The glucose values of the falling parts of the curves of all of the 11 diabetics are again plotted together in a diagram (FIG. 13). The correlation between blood and sensor values is found to be 0.9450, which proves that the sensor monitors the sugar level excellently.

We claim:

1. A process for continuously or intermittently determining the glucose concentration in subcutaneous tissue, which comprises using an enzymatic oxidation of glucose by oxygen in the presence of the enzyme glucose oxidase and determining the used amount of oxygen by means of a measuring cell, characterized in that a perfusion fluid which contains dissolved glucose oxidase, is passed continuously or intermittently at a constant rate via a supply tube through a hollow fiber provided in the subcutaneous tissue and permeable to glucose and is passed via an airtight discharge tube from the hollow fiber to a measuring cell provided outside the body, with a dialysis taking place subcutaneously whereby glucose passes via the wall of the hollow fiber from the tissue into the perfusion fluid in an amount proportional to the locally prevailing glucose concentration, and with the glucose received in the perfusion fluid being completely oxidized before reaching the measuring cell.

2. A process as claimed in claim 1 characterized in that the perfusion fluid is passed at a flow rate of 0.1–1.0 ml/hour.

3. A process as claimed in claim 1 characterized in that the perfusion fluid employed is a physiological saline solution containing the enzymes glucose oxidase and catalase in the dissolved state, the perfusion fluid is returned after passing through the measuring cell to the hollow fiber via a system comprising at least one air-permeable part, and before or after passing through the measuring cell the perfusion fluid is passed through an enzyme metering device provided outside the body, in which device a new amount of glucose oxidase and catalase is dissolved in the perfusion fluid.

4. A process as claimed in claim 3, characterized in that after passing through the measuring cell the perfusion fluid is returned to the hollow fiber via an air-permeable supply tube.

* * * * *